United States Patent [19]

Youssefyeh

[11] Patent Number: 4,748,272
[45] Date of Patent: May 31, 1988

[54] PHENOXYPHENYLACETATES FOR USE AS POTENTIAL MODULATORS OF ARICHIDONIC ACID PATHWAYS

[75] Inventor: Raymond D. Youssefyeh, Tarrytown, N.Y.

[73] Assignee: Rorer Pharmaceutical Corp., Fort Washington, Pa.

[21] Appl. No.: 891,846

[22] Filed: Aug. 1, 1986

[51] Int. Cl.$^4$ .................. A61K 31/19; A61K 31/22
[52] U.S. Cl. .................. 562/471; 546/147; 546/152; 546/238; 546/342; 548/203; 548/214; 548/215; 548/217; 548/240; 548/241; 548/494; 548/572; 549/32; 549/79; 549/469; 549/499; 562/490; 562/491
[58] Field of Search .................. 568/59, 632, 657; 562/471, 490, 491; 546/152, 172, 174, 176, 192, 237, 340; 514/183, 311, 317, 415, 430, 449, 568, 717, 569, 571, 570

[56] References Cited

U.S. PATENT DOCUMENTS

| | | | |
|---|---|---|---|
| 3,517,051 | 6/1970 | Bolhofer | 562/471 |
| 3,520,922 | 7/1970 | Wagner | 562/452 |
| 3,943,149 | 3/1976 | Hauck | 549/433 |
| 3,992,386 | 11/1976 | Schacht | 546/153 |
| 4,622,421 | 11/1986 | Terada | 562/491 |
| 4,631,287 | 12/1986 | Chakraborty | 514/312 |

FOREIGN PATENT DOCUMENTS 59-79793  5/1984  Japan .................. 562/471

OTHER PUBLICATIONS

Merck Index, 9th ed. (1976: Merck and Co., Rahway, NJ), p. 742.
Angerer, E. et al. (1979), Arch. Pharm., vol. 312, pp. 385–389.
Atkinson, D. C. et al. (1983), J. Med. Chem., vol. 26, pp. 1353–1360.

Primary Examiner—Donald G. Daus
Assistant Examiner—Mark W. Noel

[57] ABSTRACT

This invention relates to new lipoxygenase inhibitors possessing anti-inflammatory and anti-allergic properties. The present new compounds are of the formula:

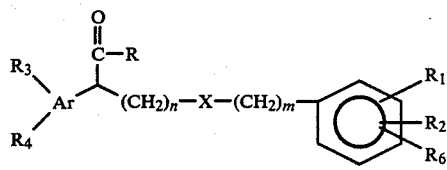

and salts thereof;
wherein
Ar is phenyl, naphthyl or sulfur, oxygen or nitrogen heterocyclic;
X is O, S, NR$_5$, or a chemical bond;
R is H, lower alkoxy, aryloxy, hydroxy, lower alkyl, aryl or lower aralkyl;
R$_1$ and R$_2$ are independently hydrogen, hydroxy, lower alkoxy, lower alkyl, aryl, aryloxy, lower aralkyl, lower aralkoxy, formyl, lower alkanoyl, benzoyl, and lower aralkanoyl;
R$_3$ and R$_4$ are independently hydrogen, halogen, hydroxy, lower alkoxy, aryloxy, lower aralkoxy, trifluoromethyl, lower carbalkoxy, carboxy, cyano, nitro, lower alkyl, lower alkenyl, lower alkynyl, aryl or lower aralkyl;
R$_5$ is H, lower alkyl, lower aralkyl or aryl;
R$_6$ is hydroxy or hydroxy-substituted lower alkyl;
n and m are independently 0, 1, 2 or 3.

11 Claims, No Drawings

PHENOXYPHENYLACETATES FOR USE AS POTENTIAL MODULATORS OF ARICHIDONIC ACID PATHWAYS

This invention relates to new chemical compounds which possess valuable therapeutic activity particularly as lipoxygenase inhibitors possessing anti-inflammatory and anti-allergic responses.

A compound having the formula:

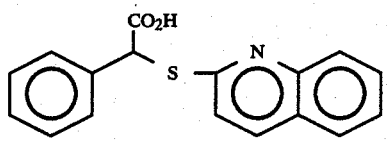

was described in *J. Org. Chem.*, 43, 2700 (1978). This reference, however, does not teach or suggest any utility for the compound.

The present new compounds are of the formula:

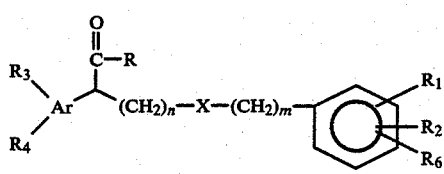

and salts thereof
wherein
Ar is phenyl, naphthyl or sulfur, oxygen or nitrogen heterocyclic;
X is O, S, $NR_5$ or a chemical bond;
R is hydroxy, lower alkoxy, aryloxy, lower aralkoxy, hydrogen, lower alkyl, aryl or lower aralkyl;
$R_1$ and $R_2$ are independently hydroxy, lower alkoxy, hydrogen, lower alkyl, aryl, aryloxy, lower aralkyl, lower aralkoxy, formyl, lower alkanoyl, benzoyl, and lower aralkanoyl;
$R_3$ and $R_4$ are independently hydrogen, halogen, hydroxy, lower alkoxy, aryloxy, lower aralkoxy, trifluoromethyl, lower carbalkoxy, carboxy, cyano, nitro, lower alkyl, lower alkenyl, lower alkynyl, aryl or lower aralkyl;
$R_5$ is hydrogen, lower alkyl, lower aralkyl, or aryl;
$R_6$ is hydroxy or hydroxy substituted lower alkyl; and
n and m are independently 0, 1, 2 or 3.

The non-heterocyclic aryl moieties of Ar, $R_1$, $R_2$, $R_3$, $R_4$, $R_5$ and aralkyl may have from 6 to 10 carbons and include phenyl, or α-or β-naphthyl, etc.

The heterocyclic rings exemplary of Ar are 5–10 membered rings containing at least one oxygen, sulfur, or nitrogen and include the so-called benzoheterocyclic rings. Exemplary heterocyclics include furan, thiophene, pyrrole, piperidine, dihydrofuran, pyridine, thiazole, piperazine, oxazole, benzofuran, tetrahydroquinoline, quinoline, isoquinoline, indole, dihydroindole, benzothiophene, dihydrobenzothiaphene, benzoxazole and similar heterocyclic rings.

The alkyl groups, either alone or within the various substitutents defined hereinabove are preferably lower alkyl, which may be straight or branched-chain and include methyl, ethyl, propyl, isopropyl, butyl, isobutyl, tert-butyl, amyl, hexyl, and the like.

Exemplary alkanoyl groups include acetyl, propionyl, butyryl, valeryl, isobutyryl, pivaloyl, neopentyl carbonyl, octanoyl, and decanoyl.

The alkenyl and alkynyl groups exemplary of $R_3$ and $R_4$ are preferably lower alkenyl and alkynyl groups which may be straight or branched-chain, wherein the multiple bond is not in the position attached to the aryl group. Exemplary alkenyl and alkynyl groups include allyl, 2-butenyl, 3-butenyl, 4-butenyl, 2-butynyl, 3-butynyl, 4-butynyl, 2-isobutenyl, 2-pentenyl, 2-pentynyl, 3-pentenyl, 3-pentynyl, 2-isopentenyl, 3-isopentenyl, and the like.

The halo atoms in halo and trihalomethyl are Cl, Br, I and F.

Additional variations in the structural formula representing the instant compounds can be effected without significantly altering the therapeutic properties, e.g., lipoxygenase inhibition. For example, the aryl groups, the phenyl groups and the heterocyclic groups can be substituted by one or more of a variety of substituents such as alkyl, aryl, halogen, hydroxy, alkoxy, aryloxy (such as phenoxy), benzyloxy, carboxy, carbalkoxy, carbamoyl, nitrilo, amino, alkylamino, dialkylamino, formyl, trihalomethyl, and nitro groups. In addition, $R_1$, $R_2$, $R_3$, $R_4$ can also be cycloalkyl groups which may be mono-or polycyclic and contain from 3 to 20 carbons. These groups include cyclopropyl, cyclopentyl, cyclohexyl, cycloheptyl, bornyl, norbornyl, indanyl and the like. These groups may be partially saturated and carry substituents such as halogen, hydroxy, lower alkyl, lower alkoxy, aminoloweralkylamino, di (lower alkyl) amino, thiol, lower alkylmercapto, nitro and trifluoromethyl.

The preferred compounds are those in which X is O, Ar is phenyl, quinoline, isoquinoline, pyrrole, indole or pyridine, R is hydroxy or lower alkoxy, $R_1$ is lower alkyl or hydrogen, $R_2$ is lower alkanoyl or hydrogen, $R_3$ is halogen or hydrogen and $R_4$ is halogen, lower alkoxy or lower alkyl. Especially preferred are those compounds wherein Ar is phenyl. The preferred halo group in $R_3$ and $R_4$ is Cl.

For those compounds wherein $R_6$ is hydroxy-substituted alkyl, it is preferred that the hydroxy group is on the α carbon to the phenyl ring.

Especially preferred are those compounds having the formula:

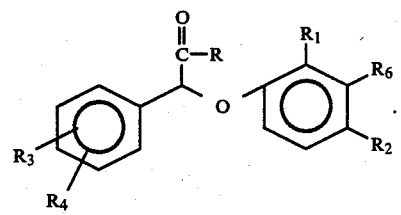

Whenever $R_6$ is hydroxy, it is preferred that $R_1$ is lower alkyl, $R_2$ is lower alkanoyl, $R_3$ is halogen or hydrogen and $R_4$ is halogen or lower alkoxy. On the other hand, when $R_6$ is hydroxy substituted lower alkyl, it is preferred that $R_1$, $R_2$ and $R_3$ are hydrogen and $R_4$ is lower alkyl or lower alkoxy.

The compounds of the present invention may contain one or more asymmetric carbon atoms and may exist in racemic and optically active forms. All of these compounds are contemplated to be within the scope of the present invention.

The present compounds can be prepared by art-recognized procedures from known compounds or readily preparable intermediates.

The products of the invention can be prepared through substitution reactions. An exemplary general procedure is as follows:

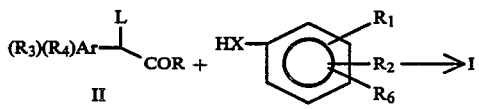

wherein Ar, R, $R_1$, $R_2$, $R_3$, are as defined above, X is O, S or $NR_5$ and L is a common leaving group such as bromine, iodine tosylate, mesylate, etc. In the case where X is O or S, the ether or thioether can also be formed under Williamson etherification reaction conditions, wherein a base such as sodium hydride, sodium hydroxide, phenyllithium, or metal, e.g., Na, Li, is used to deprotonate the alcohol or thiol. In either case, the reaction is normally effected at or near room temperature, although temperatures from 0° C up to the relux temperature of the reaction medium can be employed. The reaction is carried out in a solvent that will dissolve both reactants and in inert to both as well. Solvents, such as methylene chloride, diethyl ether, tetrahydrofuran, dioxane, chloroform, and the like can be employed.

Various substituents on the present new compounds, e.g., as defined on Ar, or the phenyl ring in compounds of Formula I can be present in the starting compounds, added to any one of the intermediates or added after formation of the final products by the known methods of substitution or conversion reactions. For example, the nitro groups can be added to the aromatic ring by nitration and the nitro group converted to other groups, such as amino by reduction, and halo by diazotization of the amino group and replacement of the diazo group. Alkanoyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono and dialkylamno groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents through the molecule of the starting material, intermediates, or the final product.

If the substituents themselves are reactive, then the substituents can themselves be protected according to the techniques known in the art. A variety of protecting groups known in the art may be employed. Examples of many of these possible groups may be found in "Protective Groups in Organic Synthesis" by T. W. Green, John Wiley and Sons, 1981.

The present new compounds form salts with acids when a basic amino function is present and salts with bases when an acid function, i.e., carboxy, is present. All such salts are useful in the isolation and/or purification of the new products. Of particular value are the pharmaceutically acceptable salts with both acids and bases. Suitable acids include, for example, hydrochloric, sulfuric, nitric, benzenesulfuric, toluenesolfonic, acetic, malic, tartaric and the like which are pharmaceutically acceptable. Basic salts for pharmaceutical use are the Na, K, Ca and Mg salts.

The compounds of the present invention can be administered to the host in a variety of forms adapted to the chosen route of administration, i.e., orally, intravenously, intramuscularly or subcutaneous, topically or inhalation routes.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparbens as preservatives, a dye as flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such a hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof, and vegetable oils, The proper fluidity can be maintained, for example, by the use of a coating such as lecithin, by the maintenance of the required particle size in the case of dispersion and by the use of surfactants. The prevention of the action of microorganism can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredients from previously sterile-filtered solution thereof The following examples further illustrate the invention.

EXAMPLE 1

Ethyl 2-bromo-2-(4-methoxyphenyl)acetate

A mixture of 16 g of Ethyl 2-(4-methoxyphenyl) acetate, and 14.6 g of N-Bromosuccinamide in 600 ml of dichloromethane was stirred at room temperture for 24 hours. It was then washed with water, dried over magnesium sulfate and evaporated to dryness to give 19.4 g of Ethyl 2-bromo-2-(4-methoxyphenyl)acetate.

EXAMPLE 2

Ethyl 2(4-methoxyphenyl)-2[3-(α-hydroxyhexy)phenoxy)acetate

To a stirred mixture of 10 g of 3-(α-hydroxyhexyl)-phenol, 7.8 g of potassium carbonate, and 4 g of potassium iodide in 400 ml of DMF was added 13.2 g of Ethyl 2-bromo-2(4-methoxyphenyl)acetate and stirring was continuted at room temperature for 40 hours. The reaction mixture was then diluted with water, extracted with ethyl acetate, dried over magnesium sulfate and evaporated to dryness. The oily residue (8 g) was chromatographed by HPLC using EtOAc-hexane (1:4) as eluent to give pure product.

EXAMPLE 3

Ethyl 2-(4-Acetyl-2-n-propyl-3-hydroxyphenoxy)-2-(4-methoxyphenyl)acetate

To a cooled stirred solution of 4.0 g of 2,4-dihydroxy-3-n-propylacetophenone and 1.6 g of anhydrous potassium carbonate in 120 ml of DMF was added 5.6 g of Ethyl 2-bromo-2-(4-methoxyphenyl)acetate and stirring was continued at room temperature for 24 hours. The reaction mixture was then diluted with water, extracted with ethyl acetate, washed with water, dried over magnesium sulfate and evaporated to dryness to give the crude product which was crystallized from EtOAc/hexane to give 1.2 g of a white solid, melting point 87°–89° C.

EXAMPLE 4

2-(4-acetyl-2-n-propyl-3-hydroxyphenoxy)-2-(4-methoxyphenyl) acetic acid

A mixture of 4.5 g of Ethyl 2-(4-acetyl-2-n-propyl-3-hydroxyphenoxy)-2-(4-methoxyphenyl)acetate and 150 ml of 1 Normal sodium hydroxide was stirred at 80° C. for 2 hours. The reaction mixture was then cooled, acidified with 1 Normal hydrochloric acid, extracted with ethyl acetate, treated with charcoal, filtered and concentrated to dryness to give an oily residue which was crystallized from EtOAc/hexane, yielding 0.9 g of product, melting point 154°–156° C.

EXAMPLE 5

Ethyl 2-(4-chlorophenyl)-2-(4-acetyl-2-n-propyl-3-hydroxyphenoxy)acetate

To a cold, stirred mixture of 8 g of 2,4-dihydroxy-3-n-propylacetophenone and 4 g of potassium carbonate in 250 ml of DMF was added 13 g of Ethyl 2-bromo-2-(4-chlorophenyl)acetate, and stirring was continued at room temperature for 48 hours. The reaction mixture was then diluted with water, extracted with ethyl acetate, dried and evaporated to dryness to give 4 g of the crude product. The crude product was then crystallized from hexane to give 2.8 g of pure product, melting point 94°–95° C.

EXAMPLE 6

2-(4-acetyl-2-n-propyl-3-hydroxyphenoxy)-2-(4-chlorophenyl)acetic acid

A mixture of 5 g of Ethyl 2-(4-acetyl-2-n-propyl-3-hydroxyphenoxy)-2-(4-chlorophenyl)acetate in 100 ml of dioxane and 15 ml of concentrated hydrochloric acid was refluxed for 70 hours. The reaction mixture was then cooled and concentrated in vacuum to give 2.6 g of the crude solid. The crude product was crystallized from EtOAc/hexane to give 1.5 g of the pure product, melting point 163°–164°.

EXAMPLE 7

Ethyl 2-(2-n-propyl-3-hydroxy-4-acetylphenoxy)-2-(3,4-dichlorophenyl)acetate

To a cooled, stirred mixture of 4 g of 2,4-dihydroxy-3-n-propylacetophenone and 2 g of potassium carbonate in 100 ml of DMF was added 7 g of Ethyl 2-bromo-2-(3,4-dichlorophenyl)acetate, and stirring was continued at room temperaure for 60 hours. The reaction mixture was then diluted with water, extracted with ethyl acetate, washed with water, dried over magnesium sulfate and evaporated to dryness to give 8 g of the crude oil, which was crystallized from hexane, yielding 1.8 g of the product, melting point 77°–79° C.

EXAMPLE 8

2-(2-n-propyl-3-hydroxy-4-acetylphenoxy)-2-(3,4-dichlorophenyl)acetic acid

A mixture of 4.8 g of Ethyl 2-(2-n-propyl-3-hydroxy-4-acetylphenoxy)-2-(3,4-dichlorophenyl)acetate in 100 ml of dioxane and 15 ml of concentrated hydrochloric acid was refluxed for 70 hours. The reaction mixture was then cooled, concentrated in vacuum to give 2.9 g of the crude solid, which was crystallized from hexane to give 1.8 g of pure product, melting point 177°–180° C.

EXAMPLE 9

Using the procedure of the foregoing examples, the following compounds can be prepared from the appropriate starting materials:
methyl 2-(3-methylphenyl)-2-[(3-α-hydroxyhexyl)-phenoxy]acetate
2-(3-methylphenyl)-2-[3-(α-hydroxyhexyl)phenoxy]acetic acid The compounds of the present invention have potent activity in regulating the activity of lipoxygenease and as such posses therapeutic value in the treatment of inflammatory conditions and allergic responses such as anaphlaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicosatetraenoic acids (HETEs). Lipoxygeneases are classified according to the position in the arachidonic acid which is oxygenated. Platelets metabolize arachidonic acid to 12-diHETE, while polymorphonuclear (PMN) leukocytes contain 5 and 15 lipoxygenases. It is known that 12-HETE and 5, 12-diHETE are chemotactic for human neutrophils and eosinophils, and may augment the inflammation process. 5-HPETE is known to be a precursor of slow-reacting substance of anaphylaxis (SRS-A). The SRS family of molecules, such as leukotrienes B, C, and D, have been shown to be potent bronchoconstrictors (see, NATURE 288, 484–486 (1980)).

The following protocol describes an assay to detect inhibitors of the lipoxygenase. Such inhibitors are believed to be capable of modulating the biosynthesis of the leukotrienes, a property believed to be useful in treating asthma and inflammatory disease states.

Protocol for Detecting Inhibitors of the Lipoxyqenase Pathway

A suspension of rat neutrophils in buffer is incubated for 3 minutes at 30° C. with [$^{14}$C]-arachidonic (AA) and Calcium Ionophore A23187. Citric acid (2M) is used to quench the reaction. Following the addition of a trace amount of ($^3$H)-5-HETE together with an excess of unlabeled 5-HETE to each tube, the mixture is extracted with chlorform/methanol. The organic layer is washed with dilute acid and an aliquot is transferred to glass tubes and dried. The residue is dissolved in a small volume of chloroform and an aliquot is spotted on silica gel TLC sheets, which are developed with an ethyl acetate/isooctane/water/acetic acid solvent system. The 5-HETE spots are visualized with iodine, cut out and placed in scintillation vials for counting. After adjusting for the extraction efficiency, the amount (pmole) of [$^{14}$C]-5-HETE in each of the tubes is quantitated. The net pmoles of 5-HETE are obtained by subtracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

TABLE I shows the concentration required for inhibition of the 5-lipoxygenases (5-LOX/$I_{50}$ μM) for representative compounds according to the present invention.

TABLE 1

| Compound Example No. | 5-LOX, $I_{50}$ |
|---|---|
| 2 | 12 |
| 3 | 2.5 |
| 4 | 6 |
| 5 | 10 |
| 6 | 3.5 |
| 7 | $I_{48}$ = 10 |
| 8 | 3.5 |

What is claimed is:

1. A compound of the formula:

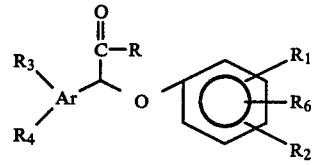

wherein Ar is phenyl or naphthyl;
R is hydroxy or lower alkoxy;
$R_1$ is lower alkyl or hydrogen;
$R_2$ is lower alkanoyl or hydrogen;
$R_3$ is halogen or hydrogen;
$R_4$ is halogen or lower alkoxy; and
$R_6$ is hydroxy or hydroxy substituted lower alkyl.

2. The compound according to claim 1 which has the formula:

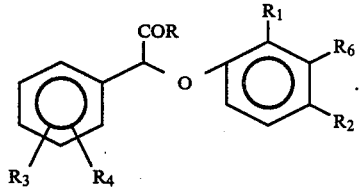

3. The compound according to claim 1 which is Ethyl 2-4-methoxyphenyl)-2-[3-(α-hydroxyhexyl)phenoxy-]acetate.

4. The compound according to claim 1 which is Ethyl 2-(4-Acetyl-2-n-propyl-3-hydroxyphenoxy)-2-(4-methoxyphenyl)acetate.

5. The compound according to claim 1 which is 2-(4-acetyl-2-n-propyl-3-hydroxyphenoxy)-2-(4-methoxyphenyl) acetic acid.

6. The compound according to claim 1 which is Ethyl 2-(4-chlorophenyl)-2-(4-acetyl-2-n-propyl-3-hydroxyphenoxy)acetate.

7. The compound according to claim 1 which is 2-(4-acetyl-2-n-propyl-3-hydroxyphenoxy)-2-(4-chlorophenyl) acetic acid.

8. The compound according to claim 1 which is Ethyl 2-(2-n-propyl-3-hydroxy-4-acetylphenoxy)-2-(3,4-dichlorophenyl)acetate.

9. The compound according to claim 1 which is 2-(2-n-propyl-3-hydroxy-4-acetylphenoxy)-2-(3,4-dichlorophenyl)acetic acid.

10. The compound according to claim 1 which is methyl 2-(3-methylphenyl)-2-[(3-α-(hydroxyhexyl)phenoxy]acetate.

11. The compound according to claim 1 which is 2-(3-methylphenyl)-2-[3-(α-hydroxyhexyl)phenoxy]acetic acid.

* * * * *